(12) United States Patent
Marnfeldt et al.

(10) Patent No.: US 6,978,780 B1
(45) Date of Patent: Dec. 27, 2005

(54) INHALATION DEVICE WITH A DOSE COUNTING UNIT

(75) Inventors: Göran Marnfeldt, Blentarp (SE); Stephen Theobald, Harboöre (DK)

(73) Assignee: AstraZeneca AB, Sodertalje (SE)

( * ) Notice: Subject to any disclaimer, the term of this patent is extended or adjusted under 35 U.S.C. 154(b) by 601 days.

(21) Appl. No.: 09/297,899

(22) PCT Filed: Mar. 30, 1999

(86) PCT No.: PCT/SE99/00540

§ 371 (c)(1),
(2), (4) Date: May 10, 1999

(87) PCT Pub. No.: WO99/49920

PCT Pub. Date: Oct. 7, 1999

(30) Foreign Application Priority Data

Mar. 30, 1998 (SE) ................................. 9801122

(51) Int. Cl.[7] ........................ A61M 15/00; A61M 16/00; B05D 7/14; B65D 83/06
(52) U.S. Cl. ................................. 128/203.15
(58) Field of Search .................. 128/200.14, 200.23, 128/200.24, 203.12, 203.15

(56) References Cited

U.S. PATENT DOCUMENTS

| | | | | |
|---|---|---|---|---|
| 5,020,527 A | * | 6/1991 | Dessertine ............. | 128/200.23 |
| 5,363,842 A | * | 11/1994 | Mishelevich et al. .. | 128/200.14 |
| 5,505,195 A | * | 4/1996 | Wolf et al. ............. | 128/203.15 |
| 5,544,647 A | | 8/1996 | Jewett et al. | |
| 5,687,710 A | * | 11/1997 | Ambrosio et al. ...... | 128/203.15 |
| 5,740,792 A | * | 4/1998 | Ashley et al. .......... | 128/203.15 |
| 5,829,434 A | * | 11/1998 | Ambrosio et al. ...... | 128/203.15 |
| 6,029,659 A | * | 2/2000 | O'Conner ............... | 128/203.12 |

FOREIGN PATENT DOCUMENTS

| | | |
|---|---|---|
| EP | 0 237 507 A1 | 9/1987 |
| EP | 0 684 047 A2 | 11/1995 |
| WO | WO 91/06334 | 5/1991 |
| WO | WO 95/26769 | 10/1995 |

OTHER PUBLICATIONS

International Search Report, Jul. 28, 1999.

* cited by examiner

*Primary Examiner*—Henry Bennett
(74) *Attorney, Agent, or Firm*—Fish & Richardson P.C.

(57) ABSTRACT

An inhaler for administering medicament by inhalation, comprising: an inhalation channel (24); a rotatable dosing unit (16) which includes at least one dosing element (18) for providing a dose of medicament to the inhalation channel (24); and a dose counting unit (42) which comprises an electronic display (57), an electrical circuit for counting each dose of medicament provided to the inhalation channel (24) and driving the display (57) so as to provide an indication as to the usage of the inhaler, the electrical circuit including at least one switch which comprises a contact element which is one of opened or closed when a dose of medicament is provided to the inhalation channel (24), and a rotatable member (45) connected to the dosing unit (16) so as to be rotatable therewith, the rotatable member (45) including at least one cam surface (51, 52) which includes at least one cam (51a, 52a), each cam (51a, 52a) on each cam surface (51, 52) being configured, on rotation of the dosing unit (16) to provide a dose of medicament to the inhalation channel (24), such as to cause movement of the contact element of the respective at least one switch and one of open or close the same.

16 Claims, 12 Drawing Sheets

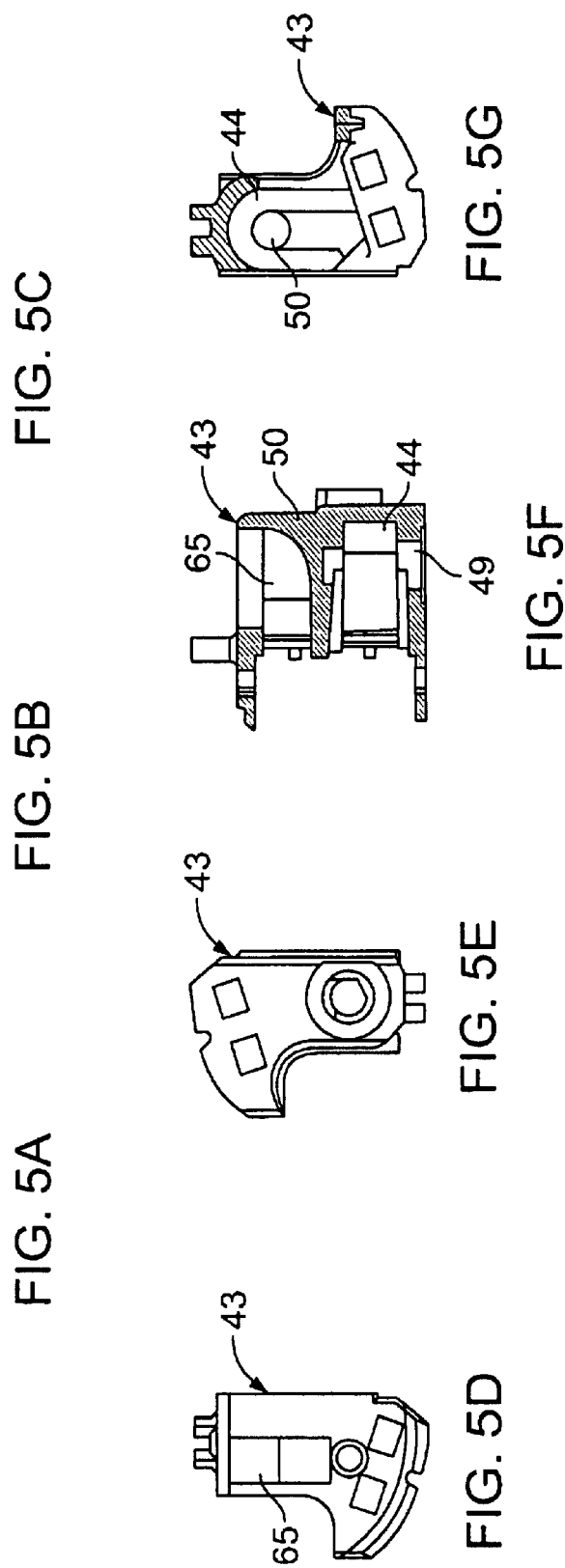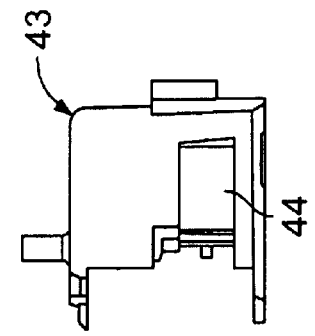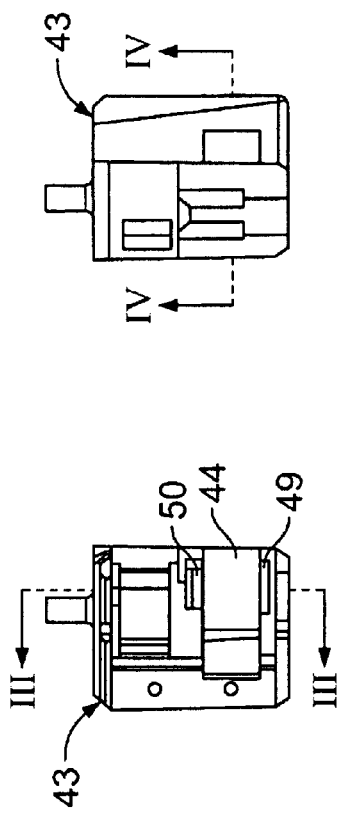

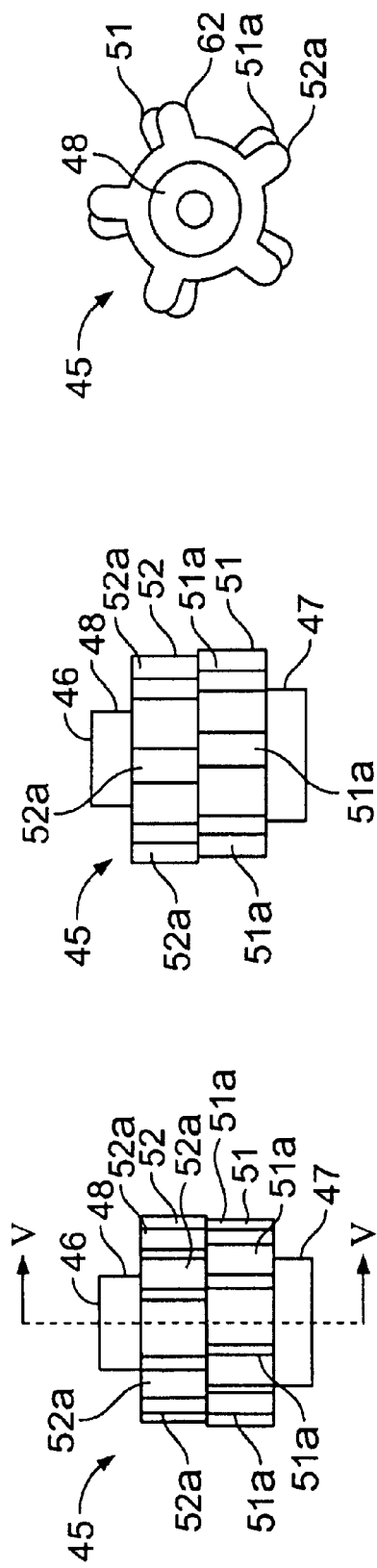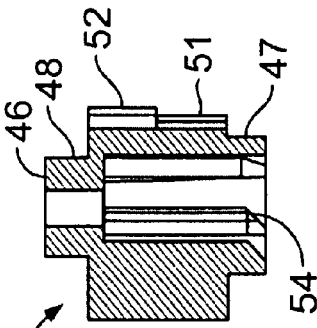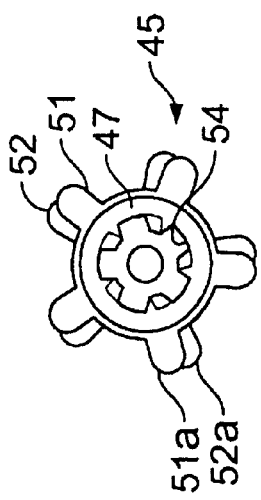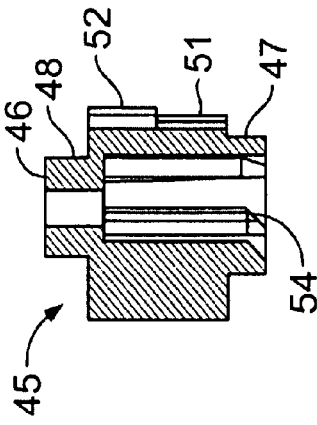

INHALATION DEVICE WITH A DOSE COUNTING UNIT

The present invention relates to an inhaler for administering medicament by inhalation, in particular a powder inhaler for administering powder containing medicament.

A number of powder inhalers are known which use different systems for introducing a dose of powder containing medicament into an air stream. Typically, the powder is inhaled into the lungs of a patient in order to treat, for example, asthma.

EP-A-0237507 discloses one such powder inhaler. This inhaler comprises an inhalation channel and a mouthpiece which includes an air chamber and an outlet nozzle, which inhalation channel and mouthpiece together define a flow path through which a stream of air is drawn during inhalation by a user. This inhaler further comprises a dosing mechanism for providing a dose of powder to the inhalation channel. During inhalation, air is first drawn into and through the inhalation channel so as to pick up powder. The stream of air containing powder is then drawn through the air chamber and out of the outlet nozzle of the mouthpiece. This inhaler still further comprises an indicating wheel which includes marking on the periphery thereof for providing an indication as to the usage of the inhaler.

Although the above-described known powder inhaler functions quite adequately, it is an aim of the present invention to provide a powder inhaler which includes an electronic dose counter for providing the user with a precise indication of either the number of doses used or the number of doses remaining.

Accordingly, the present invention provides an inhaler for administering medicament by inhalation, comprising: an inhalation channel; a rotatable dosing unit which includes at least one dosing element for providing a dose of medicament to the inhalation channel; and a dose counting unit which comprises an electronic display, an electrical circuit for counting each dose of medicament provided to the inhalation channel and driving the display so as to provide an indication as to the usage of the inhaler, the electrical circuit including at least one switch which comprises a contact element and is one of opened or closed when a dose of medicament is provided to the inhalation channel, and a rotatable member connected to the dosing unit so as to be rotatable therewith, the rotatable member including at least one cam surface which includes at least one cam, each cam on each cam surface being configured, on rotation of the dosing unit to provide a dose of medicament to the inhalation channel, such as to cause movement of the contact element of the respective at least one switch and one of open or close the same.

Preferably, the electrical circuit includes a first switch which comprises a first contact element and a second switch which comprises a second contact element and the rotatable member includes first and second cam surfaces which each include at least one cam which is configured to cause movement of a respective one of the first and second contact elements so as to one of open or close the first and second switches.

Preferably, the dosing unit includes a plurality of dosing elements and each cam surface includes a plurality of cams having the same angular spacing as the dosing elements in the dosing unit.

More preferably, the plurality of dosing elements in the dosing unit and the plurality of cams on each cam surface are angularly equi-spaced.

Preferably, the corresponding cams on the first and second cam surfaces are rotationally offset in relation to one another such that one of the first and second switches is one of opened or closed before the other.

More preferably, the cams on the first and second cam surfaces are rotationally offset such that, on rotation of the rotatable member, in a first phase of rotation one of the first and second switches is closed and the other of the first and second switches is open, in a second phase of rotation the first and second switches are closed, in a third phase of rotation the one of the first and second switches is open and the other of the first and second switches is closed and in a fourth phase of rotation the first and second switches are open, and the electrical circuit is configured to count only when this sequence of closing and opening the first and second switches is followed.

Preferably, each contact element is a resiliently-biased arm which includes a first part which rides on the respective cam surface and a second part which provides a contact pad.

More preferably, the arm is resilient and configured such that the second part thereof which provides a contact pad moves at least partly laterally over a contact surface when the first part thereof rides onto and over a cam.

More preferably, the arm includes a bend, the outer surface of which provides the second part thereof that rides on the respective cam surface.

Preferably, the dosing unit includes a shaft which includes a surface provided with one of at least one of an external or internal spline and the rotatable member includes a surface provided with the other of at least one of an external or internal spline, the splines being engaged such that the dosing unit and the rotatable member in use rotate concomitantly.

In one embodiment the electrical circuit is configured to drive the display to display the number of doses used.

In another embodiment the electrical circuit is configured to drive the display to display the number of doses remaining.

Preferably, the electrical circuit is configured to drive the display to display intermittently the number of doses remaining when a predetermined number of doses or less are remaining.

Preferably, the display is a liquid crystal display.

Preferably, the inhaler further comprises a rotatable grip portion which is in use gripped by a user and when rotated in one sense rotates the dosing unit to provide a dose of medicament to the inhalation channel.

By virtue of the present invention the user is provided by an accurate and reliable indication as to the usage of the inhaler.

The powder inhaler of the present invention may be used with any suitable form of powder, including powders introduced into the air stream in the raw state or as conglomerate, micronised or ordered mixture particles. Furthermore, the active ingredient or ingredients of the powder may be diluted with one or more substances such as lactose and may include substances for the treatment of various conditions, not necessarily respiratory conditions. Indeed, the powder can include genetic material and need not be restricted to human use only.

Medicaments suitable for administration by the powder inhaler of the present invention are any which may be delivered by inhalation and include, for example, β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

A preferred embodiment of the present invention will now be described hereinbelow by way of example only with reference to the accompanying drawings, in which.

Figure 1:
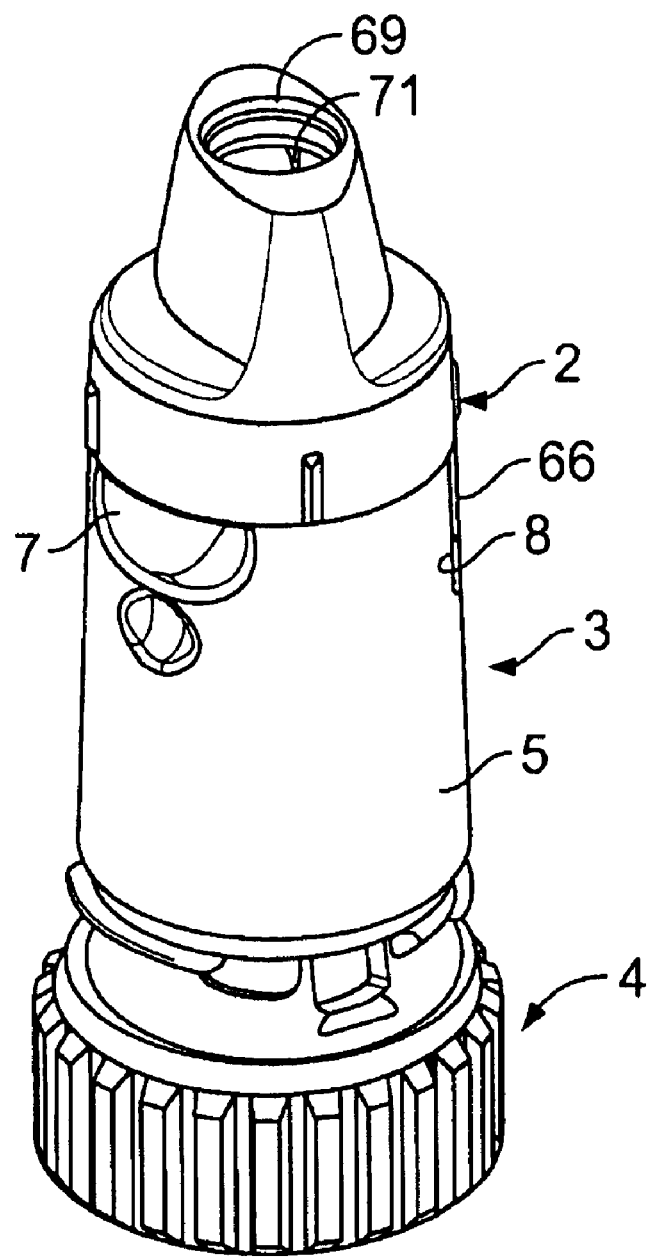
FIG. 1 illustrates a perspective view of a powder inhaler in accordance with a preferred embodiment of the present invention.
Figure 4A:
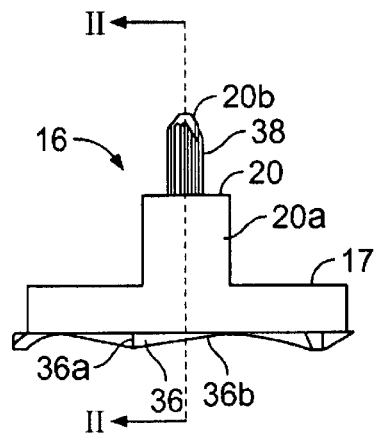
Figure 4B:
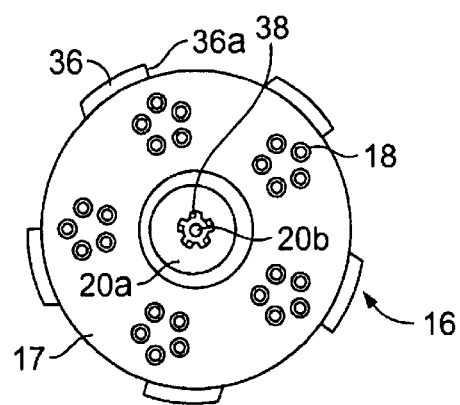
Figure 4C:
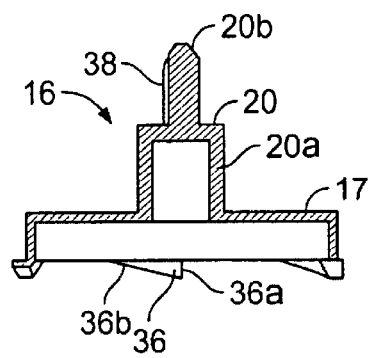
Figure 4D:
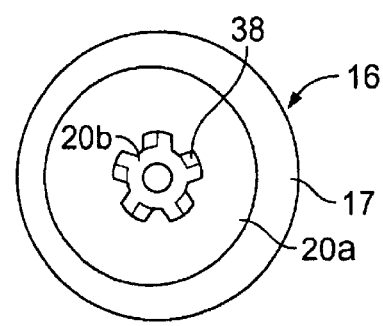
Figure 7A:
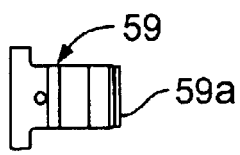
Figure 7B:
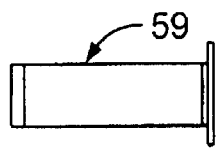
Figure 7C:
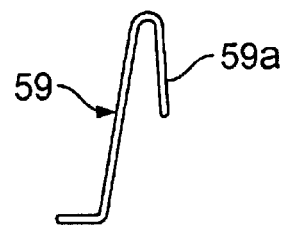
Figure 8A:
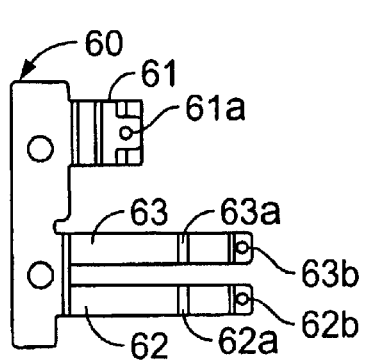
Figure 8B:
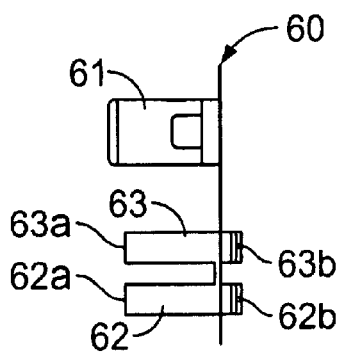
Figure 8C:
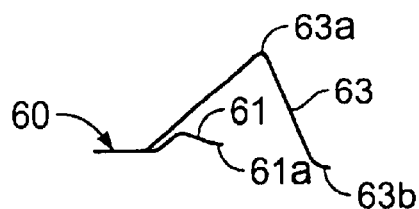
Figure 9A:
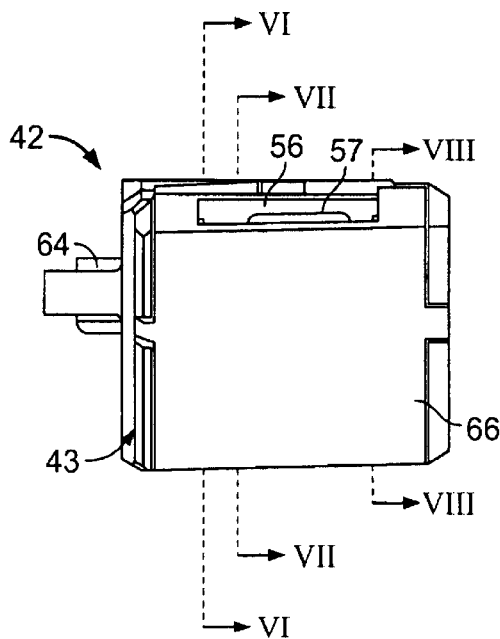
Figure 9B:
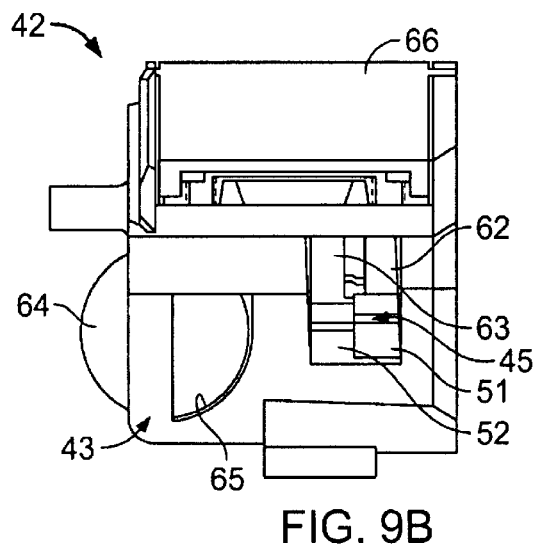
Figure 9C:
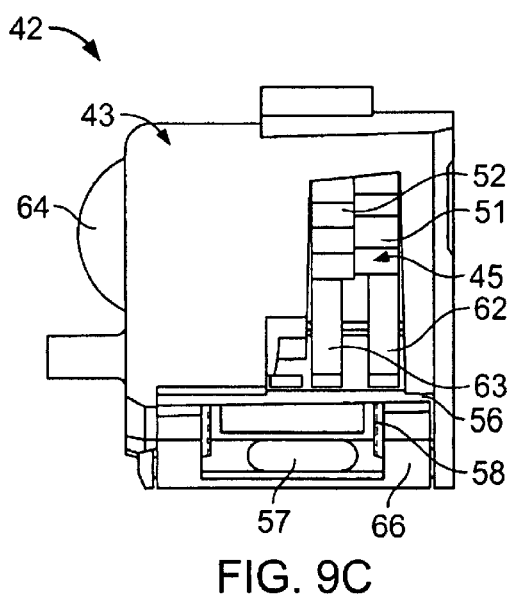
Figure 9D:
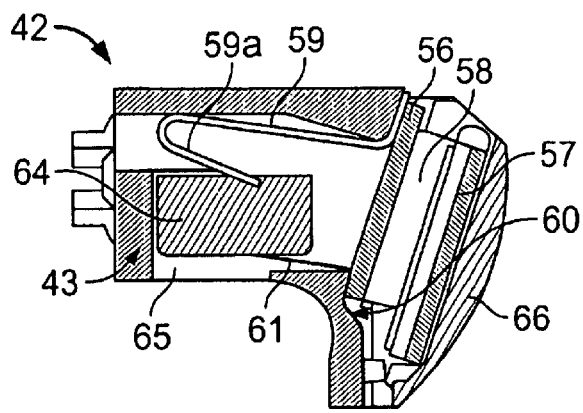
Figure 9E:
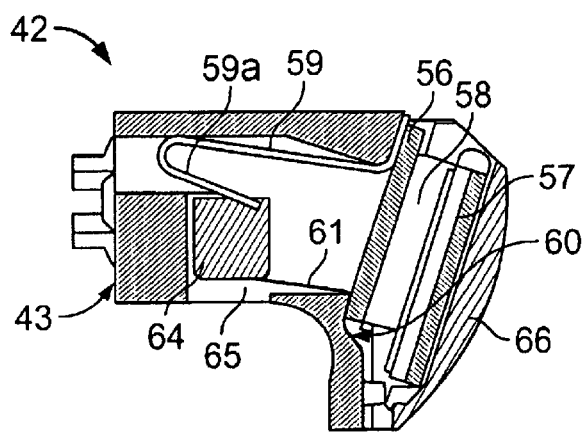
Figure 9F:
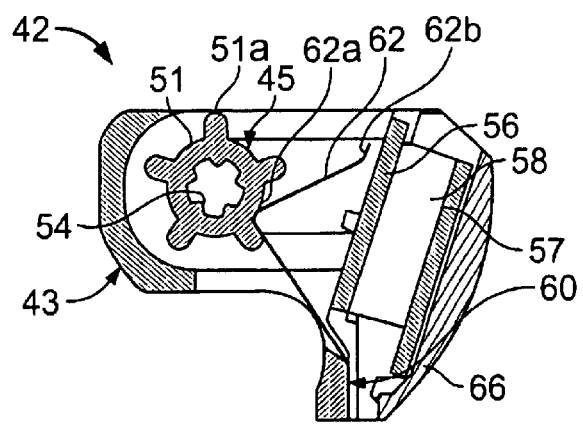
Figure 10A:
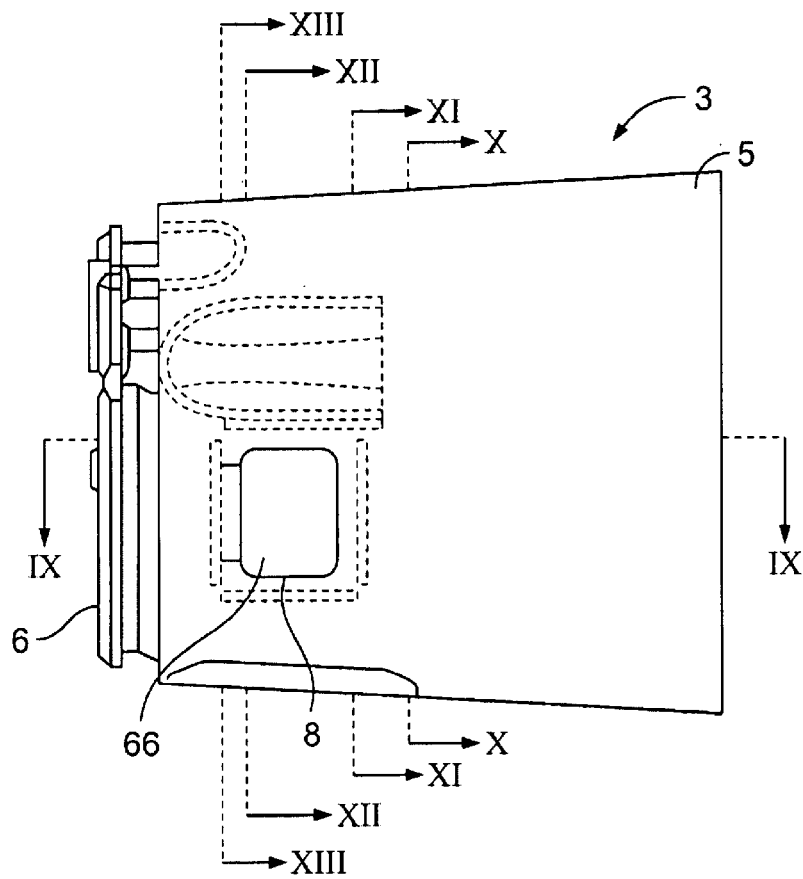
Figure 10B:
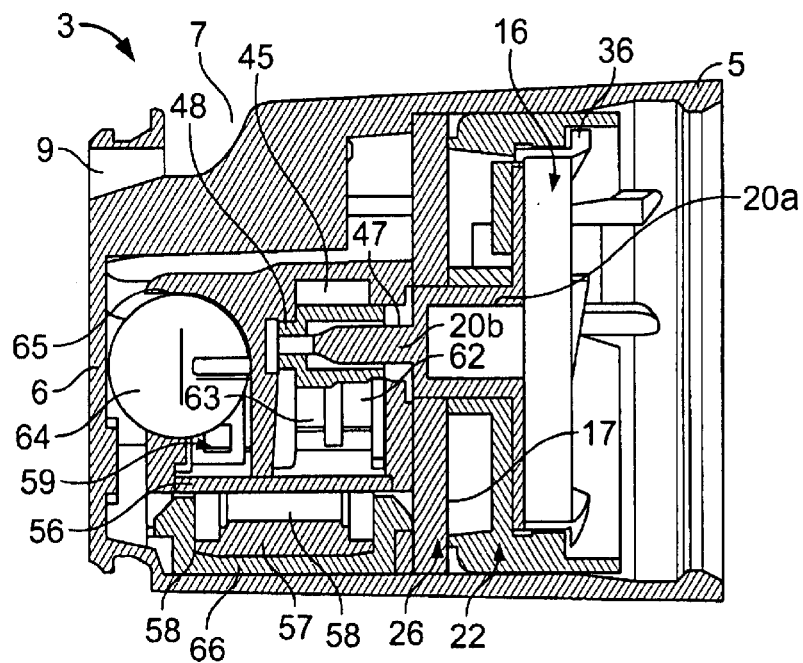
Figure 10C:
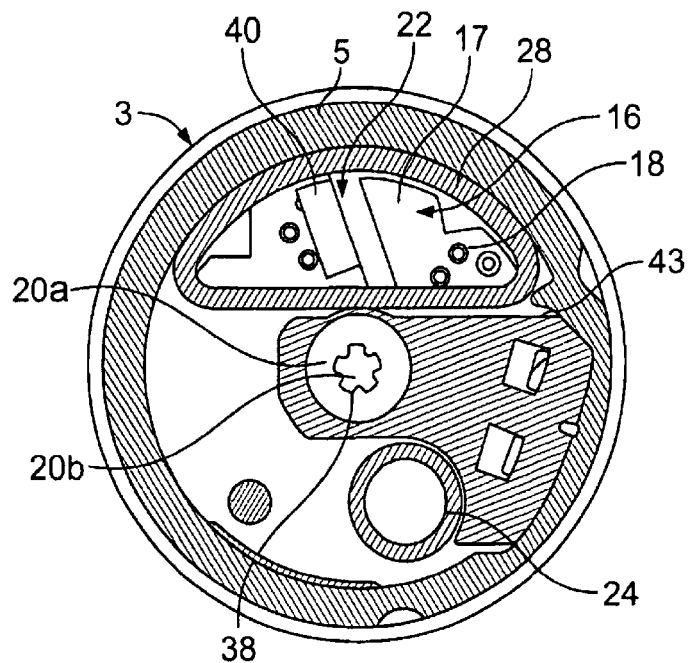
Figure 10D:
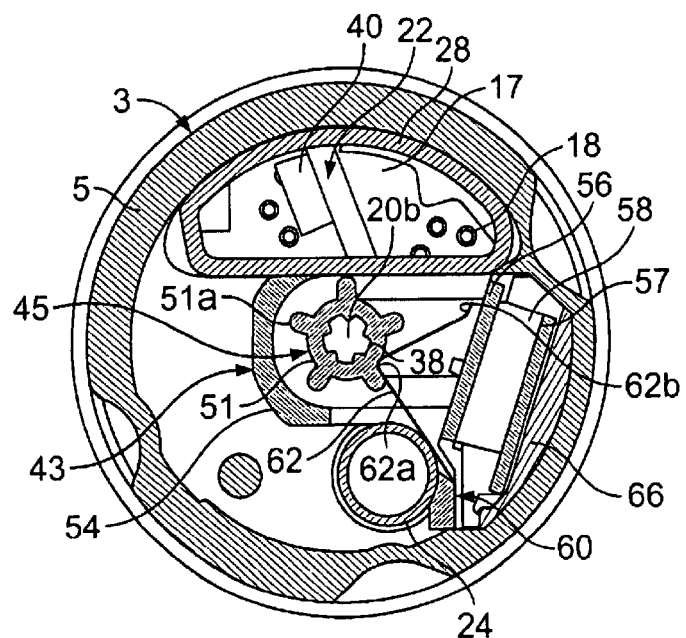
Figure 10E:
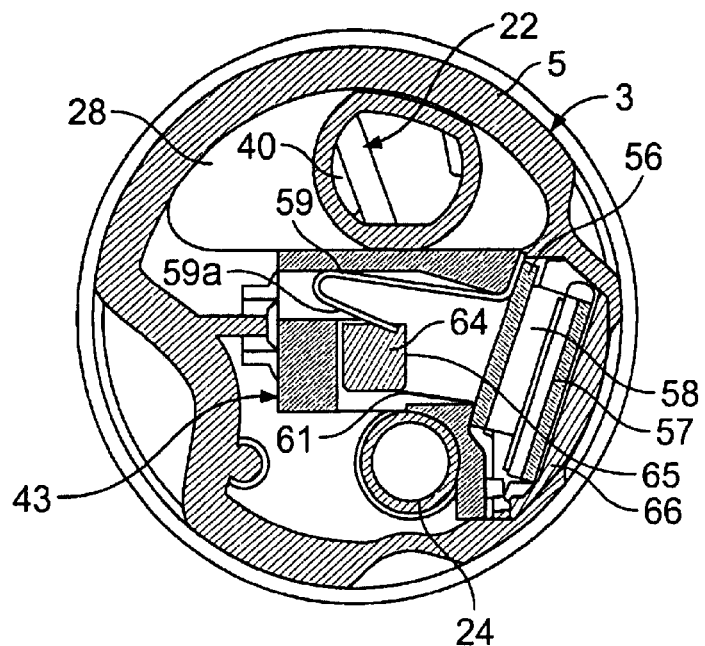
Figure 10F:
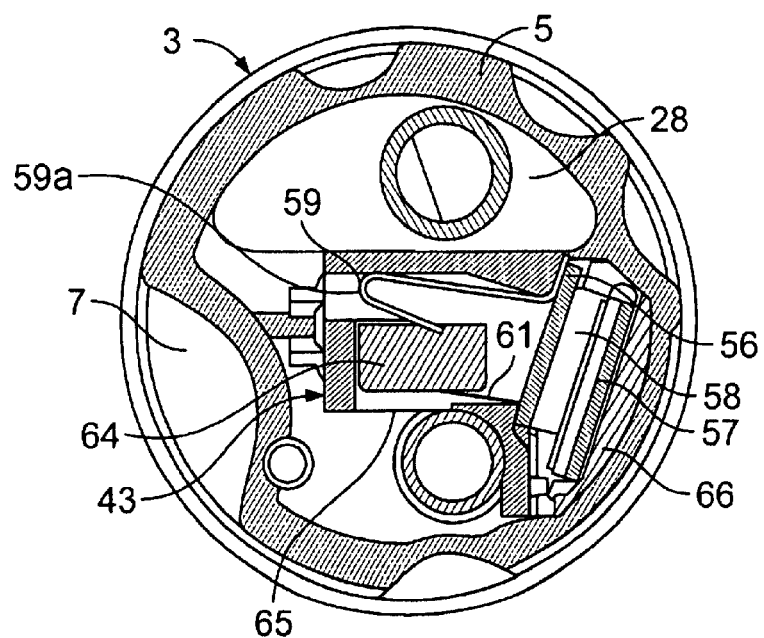

FIGS. 4(a) and (b) illustrate respectively side and plan views of the dosing unit of the inhaler of FIG. 1;

FIG. 4(c) illustrates a vertical sectional view (along section II—II in FIG. 4(a)) of the dosing unit of FIGS. 4(a) and (b);

FIG. 4(d) illustrates in enlarged scale a fragmentary plan view of the dosing unit of FIGS. 4(a) and (b);

FIGS. 5(a) to (e) illustrate respectively front, rear, side, plan and underneath plan views of the body part of the dose counting unit of the inhaler of FIG. 1;

FIG. 5(f) illustrates a vertical sectional view (along section III—III in FIG. 5(a)) of the body part of FIGS. 5(a) to (e);

FIG. 5(g) illustrates a horizontal sectional view (along section IV—IV in FIG. 5(b)) of the body part of FIGS. 5(a) to (e);

FIGS. 6(a) to (d) illustrate respectively one side, other side, plan and underneath plan views of the rotor of the dose counting unit of the inhaler of FIG. 1;

FIG. 6(e) illustrates a vertical sectional view (along section V—V in FIG. 6(a)) of the rotor of FIGS. 6(a) to (d);

FIGS. 7(a) to (c) illustrate respectively end, side and plan views of the first conductive member of the electrical device of the inhaler of FIG. 1;

FIGS. 8(a) to (c) illustrate respectively rear, side and plan views of the second conductive member of the electrical device of the inhaler of FIG. 1;

FIGS. 9(a) to (c) illustrate respectively front, one side and other side views of the dose counting unit of the inhaler of FIG. 1;

FIG. 9(d) illustrates a horizontal sectional view (along section VI—VI in FIG. 9(a)) of the dose counting unit of FIGS. 9(a) to (c);

FIG. 9(e) illustrates a horizontal sectional view (along section VII—VII in FIG. 9(a)) of the dose counting unit of FIGS. 9(a) to (c);

FIG. 9(f) illustrates a horizontal sectional view (along section VIII—VIII in FIG. 9(a)) of the dose counting unit of FIGS. 9(a) to (c);

FIG. 10(a) illustrates a side view of the inhaler body of the inhaler of FIG. 1, with the internal component parts disposed therein;

FIG. 10(b) illustrates a vertical sectional view (along section IX—IX in FIG. 10(a)) of the inhaler body of FIG. 10(a);

FIG. 10(c) illustrates a horizontal sectional view (along section X—X in FIG. 10(a)) of the inhaler body of FIG. 10(a);

FIG. 10(d) illustrates a horizontal sectional view (along section XI—XI in FIG. 10(a)) of the inhaler body of FIG. 10(a);

FIG. 10(e) illustrates a horizontal sectional view (along section XII—XII in FIG. 10(a)) of the inhaler body of FIG. 10(a); and FIG. 10(f) illustrates a horizontal sectional view (along section XIII—XIII in FIG. 10(a)) of the inhaler body of FIG. 10(a).

The inhaler comprises a mouthpiece 2, an inhaler body 3 and a rotatable grip portion 4 for operating a dosing mechanism for providing doses of powder for inhalation.

The inhaler body 3 comprises a generally cylindrical tubular member 5 which is capped by a divider 6, which in this embodiment are integrally formed. For aesthetic reasons the inhaler body 3 is an opaque moulding. The tubular member 5 includes a first opening 7 which acts as a supplementary air inlet and a second opening 8 through which an electronic display 57 is visible for providing an indication as to the usage of the inhaler. The divider 6 includes a first opening 9 which is in communication with the first opening 7 in the tubular member 5 and acts as a supplementary air inlet and second and third openings 10, 11 into which extend an inhalation channel 24 and a storage chamber 28 as will be described in more detail hereinbelow.

Within the inhaler body 3 are housed the component parts of the dosing mechanism. These component parts include a dosing unit 16 which comprises a member 17 having a planar upper surface in which a plurality of dosing elements 18 are provided and a shaft 20 which extends axially from the centre of the member 17, an inhalation unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft 20 through central openings 32, 34 in the inhalation unit 22 and the storage unit 26 respectively. When so assembled, the upper ends of the inhalation channel 24 and the storage chamber 28 pass respectively through the second and third openings 10, 11 in the divider 6. In this way, the inhalation unit 22 and the storage unit 26 are fixed in position in relation to one another and the dosing unit 16 can be rotated relative thereto.

The dosing unit 16 comprises a plurality of dosing elements 18, each in the form of a plurality of through holes, which are equi-spaced circularly about the central shaft 20. In this embodiment the dosing unit 16 includes five dosing elements 18 which are angularly spaced apart from one another by an angle of 72 degrees. The dosing unit 16 further comprises a plurality of wedge-shaped elements 36, in the same number and spacing as the dosing elements 18, disposed around the outer periphery of the member 17. Each wedge-shaped element 36 has a first, axially-directed surface 36a which faces in one sense, in this embodiment in the clockwise sense when viewed from above, and a second surface 36b which has a component which faces in the opposite, counter-clockwise sense. In use, the dosing unit 16 is rotated by rotating the grip portion 4 in the opposite sense, that is, the counter-clockwise sense when viewed from above, the grip portion 4 including a resilient member (not illustrated) which is configured to engage with the axially-directed surface 36a of a respective one of the wedge-shaped elements 36 so as to rotate the dosing unit 16 between first and second angularly-spaced positions, in this embodiment positions angularly spaced 72 degrees apart, by pushing the respective wedge-shaped element 36. On rotation of the grip portion 4 in the one, clockwise sense between the second and the first angularly-spaced positions, the dosing unit 16 remains stationary and the resilient member is located behind the axially-directed surface 36a of the adjacent wedge-shaped element 36; the resilient member riding over the second surface 36b of the adjacent wedge-shaped element 36. Further, in this embodiment, the central shaft 20 comprises a first, lower part 20a, the outer surface of which is generally cylindrical and acts as a bearing surface in the central openings 32, 34 in the inhalation unit 22 and the storage unit 26, and a second, upper part 20b which is of smaller radial dimension than the first part 20a and includes a plurality of external splines 38 on the outer surface thereof.

In this embodiment the storage unit 28 is open at the bottom such that in use powder is provided to the dosing unit 16 under the action of gravity and the inhalation unit 22 further comprises scrapers 40 which are resiliently biased against the upper surface of the member 17 in which the dosing elements 18 are provided. In this way, as the dosing unit 16 is rotated, the dosing elements 18 are filled with powder by the scrapers 40. Powder is prevented from passing through the dosing elements 18 by a plate (not illustrated) which is disposed beneath the dosing unit 16.

Within the inhaler body 3 is also housed a dose counting unit 42 for counting the number of operations of the grip portion 4 in providing doses of powder to the inhalation channel 24. The dose counting unit 42 is located on the storage unit 26 between the storage member 28 thereof and the inhalation channel 24.

The dose counting unit 42 comprises a body part 43 which includes a first cavity 44 and a rotor 45 which is disposed in the first cavity 44. The rotor 45 comprises a hollow shaft 46 which includes first and second bearing surfaces 47, 48 at opposed ends thereof, which first and second bearing surfaces 47, 48 are configured to fit respectively within lower and upper recesses 49, 50 in opposed surfaces of the first cavity 44. The first bearing surface 47 and the lower recess 49 are of different, in this embodiment larger, dimension than the second bearing surface 48 and the upper recess 50 so as to ensure that the rotor 45 is fitted in the first cavity 44 with the correct orientation. The outer surface of the shaft 46 includes first and second axially-spaced cam surfaces 51, 52, each including a plurality of cams 51a, 52a of the same number. The cams 51a, 52a on the first and second cam surfaces 51, 52 have rounded distal ends and are circumferentially equi-spaced. In this embodiment each cam surface 51, 52 includes five cams 51a, 52a which are angularly spaced apart from one another by an angle of 72 degrees, with the corresponding cams 51a, 52a on the first and second cam surfaces 51, 52 being angularly shifted by a predetermined angle, typically about 18 degrees, such that the cams 51a on the first cam surface 51 are forward of the corresponding cams 52a on the second cam surface 52 in the sense of rotation, in this embodiment in the counter-clockwise sense when viewed from above. The inner surface of the shaft 46 includes a plurality of internal splines 54 which are configured to receive the external splines 38 on the upper part 20b of the shaft 20 of the dosing unit 16 so as rotationally to fix the rotor 45 relative to the dosing unit 16, whereby the rotor 45 is rotated concomitantly with the dosing unit 16. In this embodiment the splines 38, 54 are not a tight fit but rather have a limited freedom of movement so as to allow for relatively easy inter-engagement thereof. In rotationally fixing the dosing unit 16 and the rotor 45 using splines 38, 54, as compared, for example, to forming the dosing unit 16 integrally with the rotor 45, a certain degree of tolerance is provided since the position of the rotor 45 which includes the cam surfaces 51, 52 is not dependent upon the position of the dosing unit 16.

The dose counting unit 42 further comprises an electrical device 55 which comprises a printed circuit board 56 which is mounted to the body part 43, the printed circuit board 56 including an integrated circuit for counting input pulses corresponding to the number of operations of the grip portion 4 in providing doses of powder to the inhalation channel 24 and driving an electronic display 57, an electronic display 57, in this embodiment a liquid crystal display, for displaying either the number of doses provided to the inhalation channel 24 or the number of doses remaining in the storage chamber 28 which is connected to one side 56a of the printed circuit board 56 by first and second elastomeric conducting elements 58 (so-called zebra strips) and a first conductive member 59 connected to the other side 56b of the printed circuit board 56. The first conductive member 59 is a gold-plated element and comprises a resilient arm 59a which is configured to contact one of the terminals, in this embodiment the anode terminal, of a battery cell 64. The electrical device 55 further comprises a second conductive member 60 which is mounted to the body part 43. The second conductive member 60 is a gold-plated element and comprises a first resilient arm 61 which is configured to contact the other of the terminals, in this embodiment the cathode terminal, of a battery cell 64 and includes a contact pad 61a which contacts the respective terminal on the printed circuit board 56, a second resilient arm 62 which acts as a first switch element and a third resilient arm 63 which acts as a second switch element. The second and third arms 62, 63 are identical in shape and include a bend 62a, 63a which encloses an acute angle, in this embodiment of about 72 degrees, with the bend 62a, 63a defining a knee which is acted upon by a respective one of the first and second cam surfaces 51, 52 of the rotor 45 as will be described in detail hereinbelow. The distal ends of the second and third arms 62, 63 each include contact pads 62b, 63b for contacting a respective contact on the printed circuit board 56 for making first and second switches.

The dose counting unit 42 yet further comprises a battery cell 64 which is disposed in a second cavity 65 in the body part 43. The battery cell 64 is arranged such that the anode and cathode terminals thereof contact respectively the arm 59a of the first conductive member 59 and the first arm 61 of the second conductive member 60.

The dose counting unit 42 still further comprises a window 66, in this embodiment formed of a transparent plastics material, which is fixed to the body part 43, preferably by clipping.

The window 66 fills the second opening 8 in the tubular member 5 of the inhaler body 3 so as to protect the electronic display 57 therebehind.

Figures 2A, 2B:
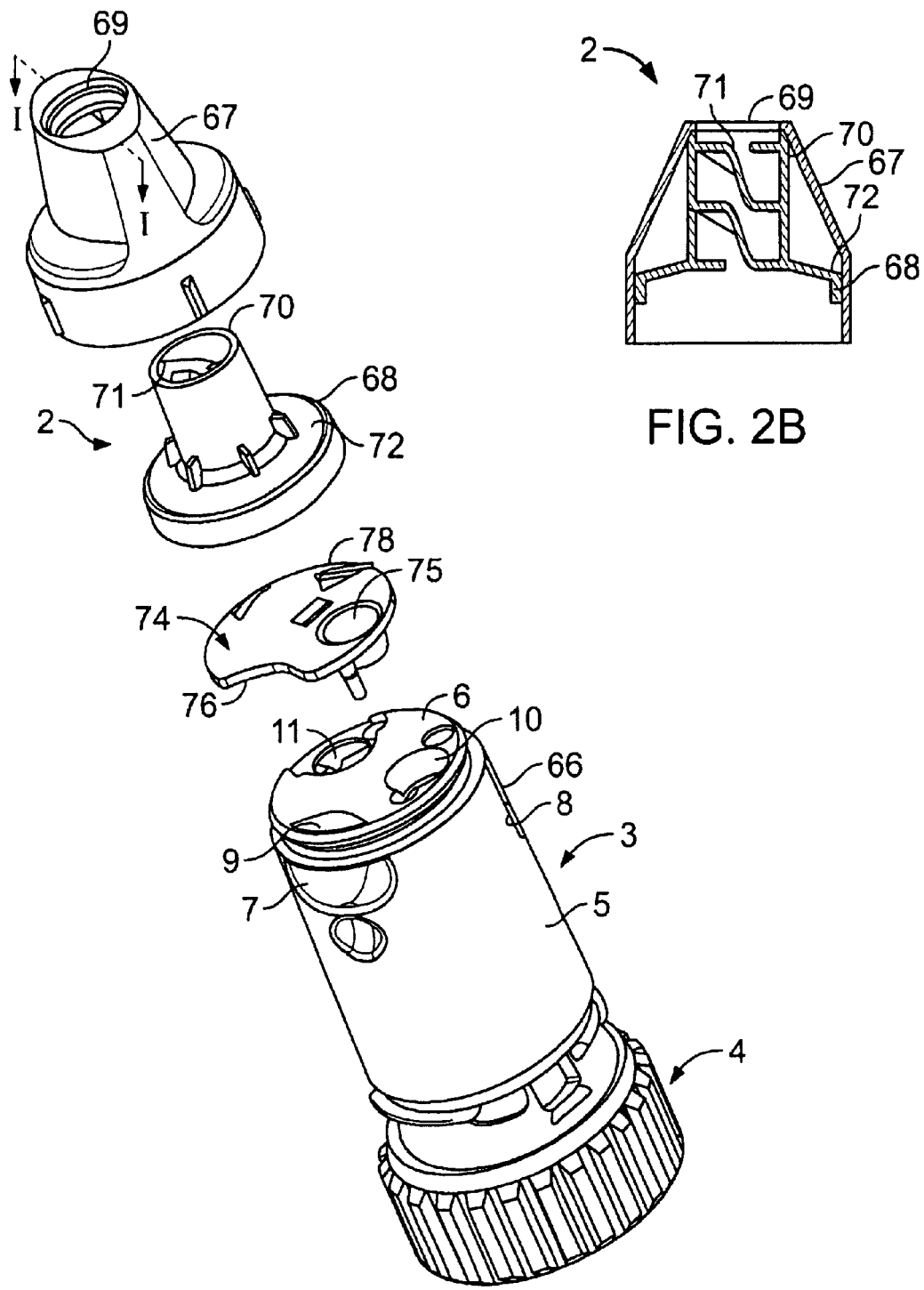
FIG. 2(a) illustrates a part exploded perspective view of the inhaler of FIG. 1.
FIG. 2(b) illustrates a vertical sectional view (along section I—I in FIG. 2(a)) of the mouthpiece of the inhaler of FIG. 1.
Figure 3:
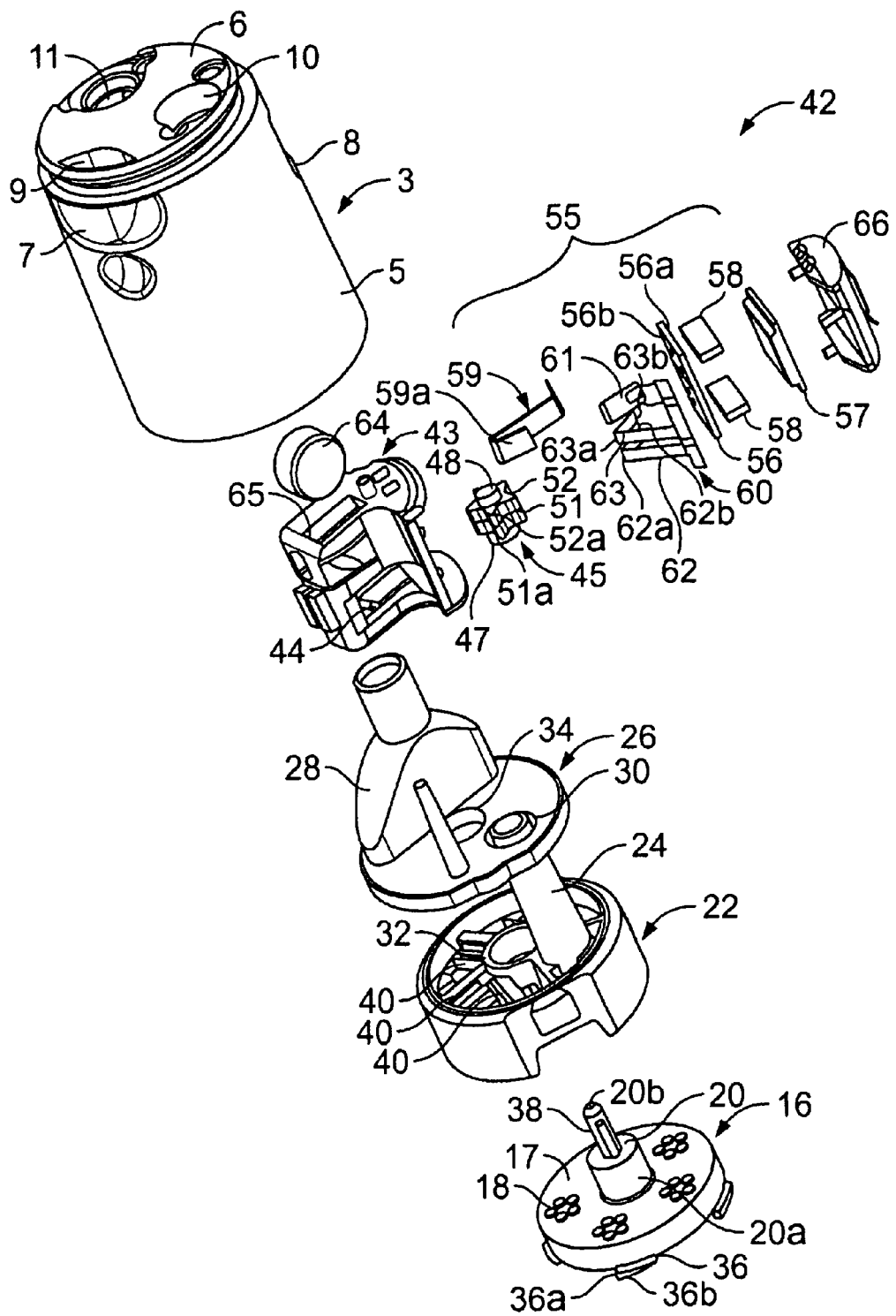
FIG. 3 illustrates an exploded perspective view of the component parts disposed within the inhaler body of the inhaler of FIG. 1.

As illustrated in FIGS. 1 and 2(a), the mouthpiece 2 is fixed to the divider 6. The mouthpiece 2 comprises first and second parts 67, 68, the first part 67 being the part which is gripped in the lips of a user and includes an outlet opening 69 through which air containing powder is in use drawn on inhalation by a user and the second part 68 being an insert fitted within the first part 67. The second part 68 comprises a tubular section 70 which includes one or more spirally or helically shaped projections 71 that act to deflect the air drawn therethrough and thereby deagglomerate any larger particles of entrained powder and a substantially radially-directed flange 72 which defines the upper surface of an air chamber that is in fluid communication with the inhalation channel 24 through which air containing powder is drawn on inhalation by a user.

The inhaler further comprises a cover plate 74 which is located above the divider 6. The cover plate 74 includes first and second openings 75, 76 which correspond respectively to the inhalation channel 24 and the supplementary air inlet 9. The cover plate 74 further comprises a powder dislodging member 78 which is configured to contact a part of the lower surface of the flange 72 which defines the upper surface of the air chamber. In this embodiment the powder dislodging member 78 is integrally formed with the cover plate 74 and comprises an arm which is formed of resilient material and biased towards the lower surface of the flange 72. In use, on rotating the mouthpiece 2 relative to the inhaler body 3, the lower surface of the flange 72 is rotated relative to the powder dislodging member 78, thereby causing powder which may have accumulated on that part of the lower surface of the flange 72 immediately upstream of the powder dislodging member 78 in a rotational sense to be removed.

In use, as described hereinabove, powder is transferred from the storage chamber 28 to one of the dosing elements 18, and, with rotation of the dosing unit 16, the one dosing element 18 provides a dose of powder to the inhalation channel 24. The dosing unit 16 is rotated by rotating the grip portion 4 in the counter-clockwise sense when viewed from above between first and second angularly-spaced positions. Initially, prior to first use of the inhaler, the display 57 displays a flashing symbol, typically a minus sign, and the user is required to operate the grip portion 4 a predetermined number of times, typically three or four times, so as to prime the dosing elements 18 in the dosing unit 16. When so primed, the display 57, which in this embodiment displays the number of doses remaining, displays an initial value which corresponds to the number of doses of powder stored in the storage chamber 28. In this state the inhaler is ready for use and subsequently after each operation of the grip portion 4 the display 57 decrements by one. Further, as a warning to the user, the value displayed on the display 57 flashes when a predetermined number of doses of powder, typically 20 doses, or less are remaining. It will, of course, be understood that in an alternative embodiment the display 57 could initially, after priming of the inhaler, display zero and thereafter display the number of times the grip portion 4 is operated.

On rotating the grip portion 4 between the first and second angularly-spaced positions the dosing unit 16 and the rotor 45 which is rotationally fixed thereto are rotated through the same angle, in this embodiment an angle of 72 degrees. In a first phase of this angular rotation of the rotor 45, the bend 62a in the second arm 62 of the second conductive member 60 which rides on the first cam surface 51 of the rotor 45 rides up onto one of the cams 51a on that cam surface 51 causing the bend 62a and hence the distal end of the second arm 62 to be deflected outwardly such that the contact pad 62b thereof contacts a contact on the printed circuit board 56 so as to make a first switch. Whilst making contact with the contact on the printed circuit board 56, the contact pad 62b moves laterally thereover so as to ensure a good contact, even if, for example, powder had deposited on the contact. In a second phase of this angular rotation of the rotor 45, with the bend 62a in the second arm 62 of the second conductive member 60 on the one of the cams 51a on the first cam surface 51 and the contact pad 62b contacting the one contact on the printed circuit board 56, the bend 63a in the third arm 63 of the second conductive member 60 which rides on the second cam surface 52 of the rotor 45 rides up onto the corresponding one of the cams 52a on that cam surface 52 causing the bend 63a and hence the distal end of the third arm 63 to be deflected outwardly such that the contact pad 63b thereof contacts another contact on the printed circuit board 56 so as to make a second switch. Similarly to the contact pad 62b of the second arm 62, whilst making contact with the respective contact on the printed circuit board 56, the contact pad 63b of the third arm 63 moves laterally thereover so as to ensure a good contact. In a third phase of this rotation of the rotor 45, with the bend 63a in the third arm 63 of the second conductive member 60 on the one of the cams 52a on the second cam surface 52 and the contact pad 63b contacting the other contact on the printed circuit board 56, the bend 62a in the second arm 62 of the second conductive member 60 rides off the one of the cams 51a on the first cam surface 51 whereby the bend 62a and hence the distal end of the second arm 62 move inwardly such that the contact pad 62b thereof no longer contacts the one contact on the printed circuit board 56 so as to open the first switch. In a fourth phase of this rotation of the rotor 45, the bend 63a in the third arm 63 of the second conductive member 60 rides off the one of the cams 52a on the second cam surface 52 whereby the bend 63a and hence the distal end of the third arm 63 move inwardly such that the contact pad 63b thereof no longer contacts the other contact on the printed circuit board 56 so as to open the second switch. In this way, on rotating the grip portion 4 of the inhaler to provide a dose of powder to the inhalation channel 24, the switches provided by the second and third arms 62, 63 of the second conductive member 60 follow the sequence open-open, closed-open, closed-closed, open-closed and open-open. In this embodiment the electrical device 55 is configured to count only when the above sequence is followed.

In providing the electrical device 55 of the dose counting unit 42 with two switches which have to be closed in order for the operation of the grip portion 4 to be counted, the dose counting circuit is more reliable than if the electrical device 55 were to include only one switch since there is a much reduced risk of two switches as opposed to one switch being inadvertently made to record a count if the inhaler were subjected to a sudden shock, for example, as when dropped onto a hard surface. Further, by configuring the dose counting circuit only to count when the switches follow the above-mentioned sequence, it is possible to ensure that the dose counting circuit does not erroneously count as may happen if the dose counting circuit were configured to count merely when both switches were simultaneously made, which, although unlikely, could possibly occur if the inhaler were to experience a sudden shock, for example, as when dropped onto a hard surface.

Finally, it will be understood that the present invention has been described in its preferred embodiment and can be modified in many different ways without departing from the scope of the appended claims.

What is claimed is:

1. An inhaler for administering medicament by inhalation, comprising:

an inhalation channel;

a rotatable dosing unit which includes at least one dosing element for providing a dose of medicament to the inhalation channel; and a dose counting unit which comprises an electronic display that displays usage of said inhaler, an electrical circuit for counting each dose of medicament provided to the inhalation channel and driving the display so as to provide an indication as to said usage of the inhaler, the electrical circuit including at least one switch which comprises a contact element that is movable between a first open position and a second closed position when a dose of medicament is provided to the inhalation channel, ad a rotatable member connected to the dosing unit so as to be rotatable therewith, the rotatable member including at least one cam surface which includes at least one cam, each cam on each cam surface being configured, on rotation of the dosing unit to provide a dose of medicament to the inhalation channel, to be in physical contact with said contact element and cause movement of the contact element of said at least one switch between said first open position and said second closed position.

2. The inhaler of claim 1, wherein the electrical circuit includes a first switch which comprises a first contact element and a second switch which comprises a second contact element and the rotatable member includes first and second cam surfaces which each include at least one cam which is configured to cause movement of a respective one of the first and second contact elements from one said position to another said position.

3. The inhaler of claim 1, wherein the dosing unit includes a plurality of dosing elements and each cam surface includes a plurality of cams having the same angular spacing as the dosing elements in the dosing unit.

4. The inhaler of claim 3, wherein the plurality of dosing elements in the dosing unit and the plurality of cams on each cam surface are angularly equi-spaced.

5. The inhaler of claim 2, wherein the corresponding cams on the first and second cam surfaces are rotationally offset in relation to one another such that one of the first and second switches is one of opened or closed before the other.

6. An inhaler for administering medicament by inhalation, comprising:

an inhalation channel;

a rotatable dosing unit which includes at least one dosing element for providing a dose of medicament to the inhalation channel; and a dose counting unit which comprises an electronic display that displays usage of said inhaler, an electrical circuit for counting each dose of medicament provided to the inhalation channel and driving the display so as to provide an indication as to said usage of the inhaler, the electrical circuit including at least one switch which comprises a contact element that is movable between a first open position and a second closed position when a dose of medicament is provided to the inhalation channel, and a rotatable member connected to the dosing unit so as to be rotatable therewith, the rotatable member including at least one cam surface which includes at least one cam, each cam on each cam surface being configured, on rotation of the dosing unit to provide a dose of medicament to the inhalation channel, to cause movement of the contact element of the respective at least one switch between said first open position and said second closed position, wherein the electrical circuit includes a first switch which comprises a first contact element and a second switch which comprises a second contact element and the rotatable member includes first and second cam surfaces which each include at least one cam which is configured to cause movement of a respective one of the first and second contact elements from one said position to another said position, wherein the corresponding cams on the first and second cam surfaces are rotationally offset in relation to one another such that one of the first and second switches is one of opened or closed before the other, wherein the cams on the first and second cam surfaces are rotationally offset such that, on rotation of the rotatable member, in a first phase of rotation one of the first and second switches is closed and the other of the first and second switches is open, in a second phase of rotation the first and second switches are closed, in a third phase of rotation the one of the first and second switches is open and the other of the first and second switches is closed and in a fourth phase of rotation the first and second switches are open, and the electrical circuit is configured to count only when this sequence of closing and opening the first and second switches is followed.

7. The inhaler of claim 1, wherein each contact element is a resiliently-biased arm which includes a first part which rides on the respective cam surface and a second part which provides a contact pad.

8. The inhaler of claim 7, wherein the arm is resilient and configured such that the second part thereof which provides a contact pad moves at least partly laterally over a contact surface when the first part thereof rides onto and over a cam.

9. The inhaler of claim 7, wherein the arm includes a bend, the outer surface of which rides on the respective cam surface.

10. The inhaler of claim 1, wherein the dosing unit includes a shaft which includes a surface provided with one of at least one of an external or internal spline and the rotatable member includes a surface provided with the other of at least one of an external spline, the splines being engaged such that the dosing unit and the rotatable member in use rotate concomitantly.

11. The inhaler of claim 1, wherein the electrical circuit is configured to drive the display to display the number of doses used.

12. The inhaler of any claim 1, wherein the electrical circuit is configured to drive the display to display the number of doses remaining.

13. The inhaler of claim 12, wherein the electrical circuit is configured to drive the display to display intermittently the number of doses remaining when a predetermined number of doses or less are remaining.

14. The inhaler of claim 1, wherein the display is a liquid crystal display.

15. The inhaler of any of claim 1, further comprising a rotatable grip portion which is in use gripped by a user and when rotated in one sense rotates the dosing unit to proved a dose of medicament to the inhalation channel.

16. An inhaler for administering medicament by inhalation, comprising:

a housing member extending along a longitudinal axis, said housing member having an opening;

an inhalation channel member within said housing member extending substantially parallel to said longitudinal axis, said inhalation channel member having an inlet, a middle portion, and an outlet portion;

a rotatable dosing unit within said housing which includes at least one dosing element for providing a dose of medicament to said inlet of said inhalation channel member; and a dose counting unit including a rotatable member connected to the dosing unit so as to be rotatable therewith, said rotatable member having a cam and being located adjacent to said middle portion within said housing said dose counting unit also including an electronic circuit that includes a switch with a contact element located within the path of travel of said cam so as to be displaced between a first open position and a second closed position when a dose of medicament is provided to the inhalation channel, said circuit counting doses provided to said inhalation channel, said dose counting unit including an electronic display that is aligned with said opening in said housing, is connected to said electrical circuit and displays an indication of doses supplied to said inhalation channel of said inhaler.

* * * * *